(12) United States Patent
Shibuya et al.

(10) Patent No.: US 12,070,364 B2
(45) Date of Patent: Aug. 27, 2024

(54) POSITION DETECTION MARKER

(71) Applicant: TDK CORPORATION, Tokyo (JP)

(72) Inventors: Tomohiko Shibuya, Tokyo (JP); Yu Hotta, Tokyo (JP); Takato Fukui, Tokyo (JP)

(73) Assignee: TDK CORPORATION, Tokyo (JP)

( * ) Notice: Subject to any disclaimer, the term of this patent is extended or adjusted under 35 U.S.C. 154(b) by 0 days.

(21) Appl. No.: 17/964,826

(22) Filed: Oct. 12, 2022

(65) Prior Publication Data

US 2023/0117248 A1 Apr. 20, 2023

(30) Foreign Application Priority Data

Oct. 18, 2021 (JP) .................................. 2021-170292

(51) Int. Cl.
*A61B 90/00* (2016.01)
*G01R 33/58* (2006.01)

(52) U.S. Cl.
CPC .............. *A61B 90/39* (2016.02); *G01R 33/58* (2013.01); *A61B 2090/3958* (2016.02)

(58) Field of Classification Search
CPC ............ A61B 90/39; A61B 2090/3958; G01R 33/0094; G01R 33/10; G01R 33/28; G01R 33/58
See application file for complete search history.

(56) References Cited

U.S. PATENT DOCUMENTS

| | | | | |
|---|---|---|---|---|
| 5,752,514 A * | 5/1998 | Okamura | ............... | A61B 5/242 324/260 |
| 6,522,908 B1 * | 2/2003 | Miyashita | ............ | A61B 5/0064 600/409 |
| 2004/0242993 A1 * | 12/2004 | Tajima | ................. | G01R 33/285 600/417 |
| 2006/0189898 A1 * | 8/2006 | Nitzan | ..................... | A61B 5/06 600/587 |
| 2010/0056901 A1 | 3/2010 | Randell | | |
| 2010/0305402 A1 * | 12/2010 | Shachar | ................ | A61B 5/062 335/297 |
| 2015/0035533 A1 | 2/2015 | Lips | | |
| 2015/0112189 A1 * | 4/2015 | Carron | ................ | A61B 5/6861 600/424 |
| 2016/0324583 A1 * | 11/2016 | Kheradpir | .............. | A61B 46/10 |
| 2017/0352457 A1 * | 12/2017 | Kubota | ..................... | H01F 5/04 |

FOREIGN PATENT DOCUMENTS

| | | | |
|---|---|---|---|
| JP | 2001037732 A | | 2/2001 |
| JP | 2002253531 A | * | 9/2002 |
| JP | 4029313 B2 | * | 1/2008 |
| JP | 2020198925 A | | 12/2020 |

OTHER PUBLICATIONS

Extended European Search Report dated Feb. 24, 2033 in EPO Application 22201879.8 (8 pages).

* cited by examiner

*Primary Examiner* — Baisakhi Roy

(74) *Attorney, Agent, or Firm* — YOUNG LAW FIRM, P.C.

(57) ABSTRACT

Disclosed herein is a position detection marker that includes a magnetic field source that generates magnetism, an MRI marker that can be detected by a magnetic resonance imaging method, and a holding part that fixes a relative positional relation between the magnetic field source and the MRI marker.

8 Claims, 5 Drawing Sheets

POSITION DETECTION MARKER

BACKGROUND OF THE INVENTION

Field of the Invention

The present invention relates to a position detection marker and, more particularly, to a position detection marker capable of being used for both a magnetic measuring apparatus and a magnetic resonance imaging apparatus.

Description of Related Art

A magnetic measuring apparatus for measuring magnetic field distribution in a predetermined space or plane has a plurality of magnetic sensors. Magnetic measuring apparatuses described in JP 2001-037732A and JP 2020-198925A use a position detection marker to recognize the relative positional relation between the plurality of magnetic sensors and an object to be measured.

However, the position detection markers described in JP 2001-037732A and JP 2020-198925A are constituted by a coil and thus cannot be photographed by a magnetic resonance imaging method. Thus, when the same object to be measured is measured by both the magnetic measuring apparatus and a magnetic resonance imaging apparatus, an image generated by the magnetic measuring apparatus and an image generated by the magnetic resonance imaging apparatus cannot be superimposed accurately.

SUMMARY

It is therefore an object of the present invention to provide a position detection marker capable of being used both for the magnetic measuring apparatus and magnetic resonance imaging apparatus.

A position detection marker according to the present invention includes: a magnetic field source that generates magnetism; an MRI marker that can be detected by a magnetic resonance imaging method; and a holding part that fixes the relative positional relation between the magnetic field source and the MRI marker.

According to the present invention, the magnetic field source which is a marker for a magnetic measuring apparatus and the MRI marker which is a marker for a magnetic resonance imaging apparatus are fixed by the holding part, thus making it possible to accurately superimpose an image generated by the magnetic measuring apparatus and an image generated by the magnetic resonance imaging apparatus.

In the present invention, the magnetic field source may be a coil. The coil allows generation of an AC magnetic field and is thus suitable as a marker for the magnetic measuring apparatus. In this case, the position detection marker according to the present invention may further include a connector to/from which a cable can be attached/detached. This allows the cable to be detached when measurement is performed using the magnetic resonance imaging apparatus, so that heat generation in the coil can be prevented. Further, the MRI marker may be disposed in the inner diameter area of the coil. This makes it possible to make the generation position of the AC magnetic field and the position of the MRI marker coincide with each other.

In the present invention, the holding part may have a configuration allowing attachment/detachment of the magnetic field source and MRI marker. This facilitates the exchange of the magnetic field source and MRI marker, improving maintainability. In this case, the holding part may include a housing part housing therein the magnetic field source and MRI marker and a lid part closing the housing part, and the housing part and lid part may be fixed to each other by screw engagement or claw engagement. This facilitates detachment of the lid part.

As described above, according to the present invention, there can be provided a position detection marker capable of being used for both the magnetic measuring apparatus and magnetic resonance imaging apparatus.

BRIEF DESCRIPTION OF THE DRAWINGS

The above and other objects, features and advantages of this invention will become more apparent by reference to the following detailed description of the invention taken in conjunction with the accompanying drawings, wherein.

DETAILED DESCRIPTION OF THE EMBODIMENTS

Preferred embodiments of the present invention will now be explained in detail with reference to the drawings.

Figure 1:
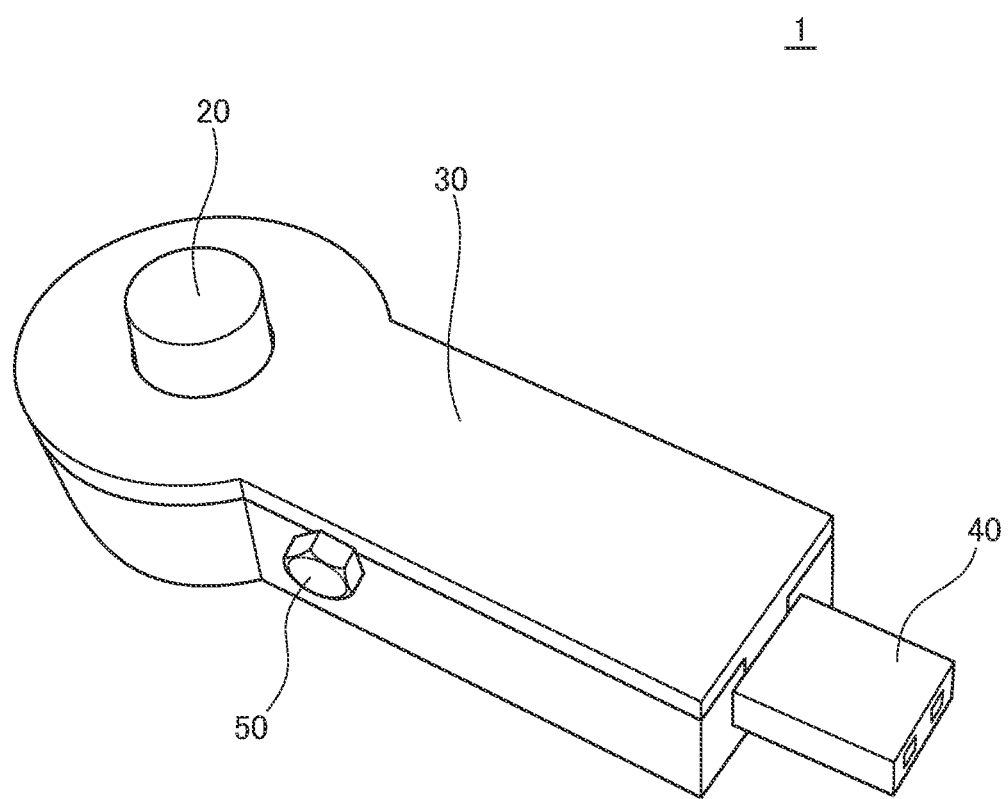
FIG. 1 is a schematic perspective view illustrating the outer appearance of a position detection marker 1 according to an embodiment of the present invention.
Figure 2:
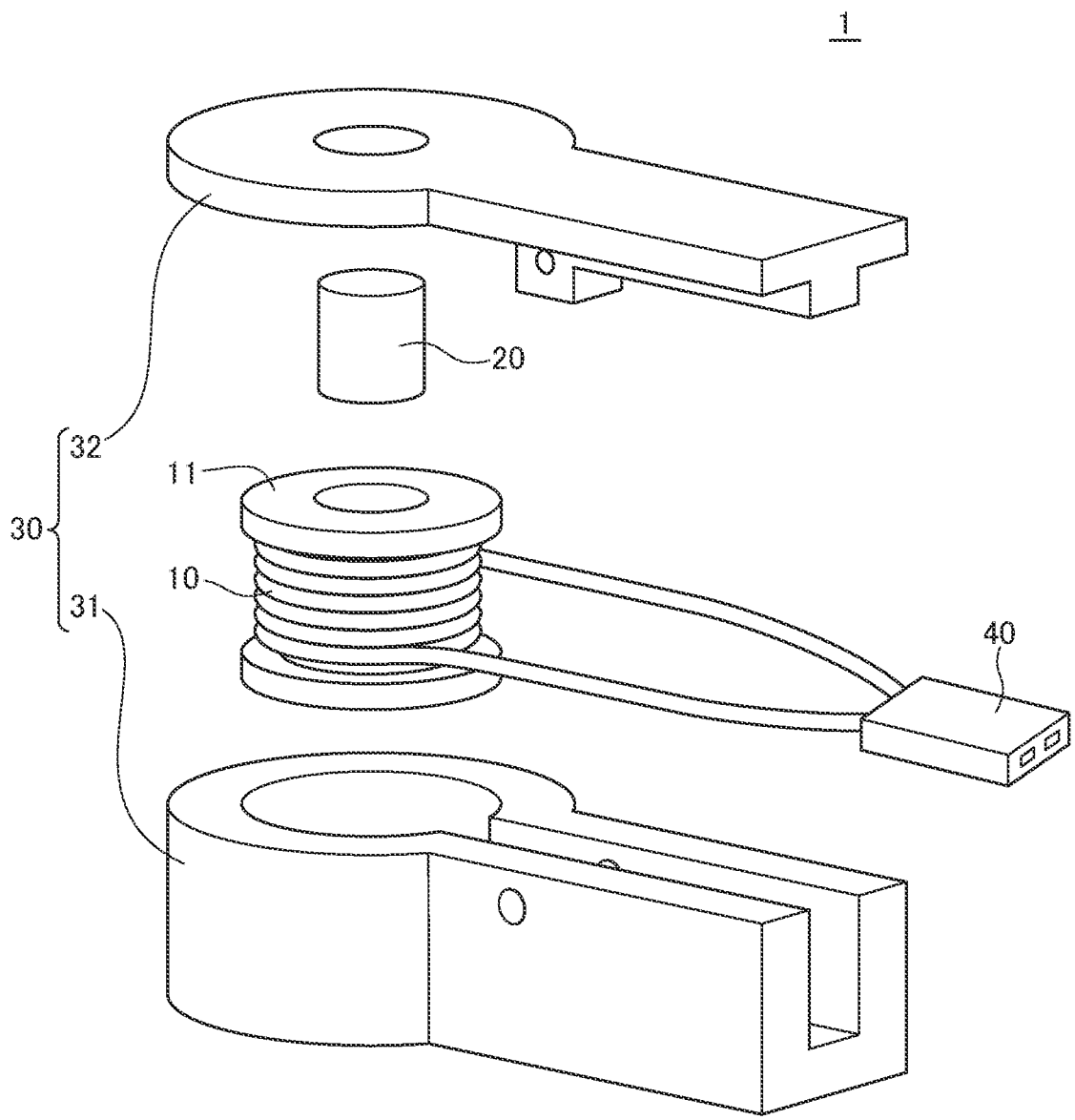
FIG. 2 is a schematic exploded perspective view of the position detection marker 1.

FIG. 1 is a schematic perspective view illustrating the outer appearance of a position detection marker 1 according to an embodiment of the present invention. FIG. 2 is a schematic exploded perspective view of the position detection marker 1.

As illustrated in FIGS. 1 and 2, the position detection marker 1 according to the present embodiment includes a coil 10 serving as a magnetic field source, an MRI marker 20, and a holding part 30 holding the coil 10 and MRI marker 20. The coil 10 is formed by a wire wound around a bobbin 11, and both ends thereof are connected to a connector 40. Thus, when an AC is supplied to the coil 10 through an external cable connected to the connector 40, an AC magnetic field can be generated from the coil 10. The MRI marker 20 is a capsule or a tablet made of a moisture-containing substance so as to be detected by a magnetic resonance imaging method and is inserted into a cylindrical winding core part of the bobbin 11. Accordingly, the MRI marker 20 is disposed in the inner diameter area of the coil 10.

The holding part 30 fixes the relative positional relation between the coil 10 and the MRI marker 20 and includes a housing part 31 housing therein the coil 10 and MRI marker 20 and a lid part 32 closing the housing part 31. As illustrated in FIG. 2, the housing part 31 and lid part 32 each have a screw hole, and a screw 50 is screwed into the screw holes to fix the housing part 31 and lid part 32. However, in the example illustrated in FIG. 2, the MRI marker 20 is inserted into the winding core part of the bobbin 11 wound with the coil 10, whereby the relative positional relation between the coil 10 and the MRI marker 20 is fixed, so that, in this case, the bobbin 11 may be regarded as a "holding part".

Figure 3:
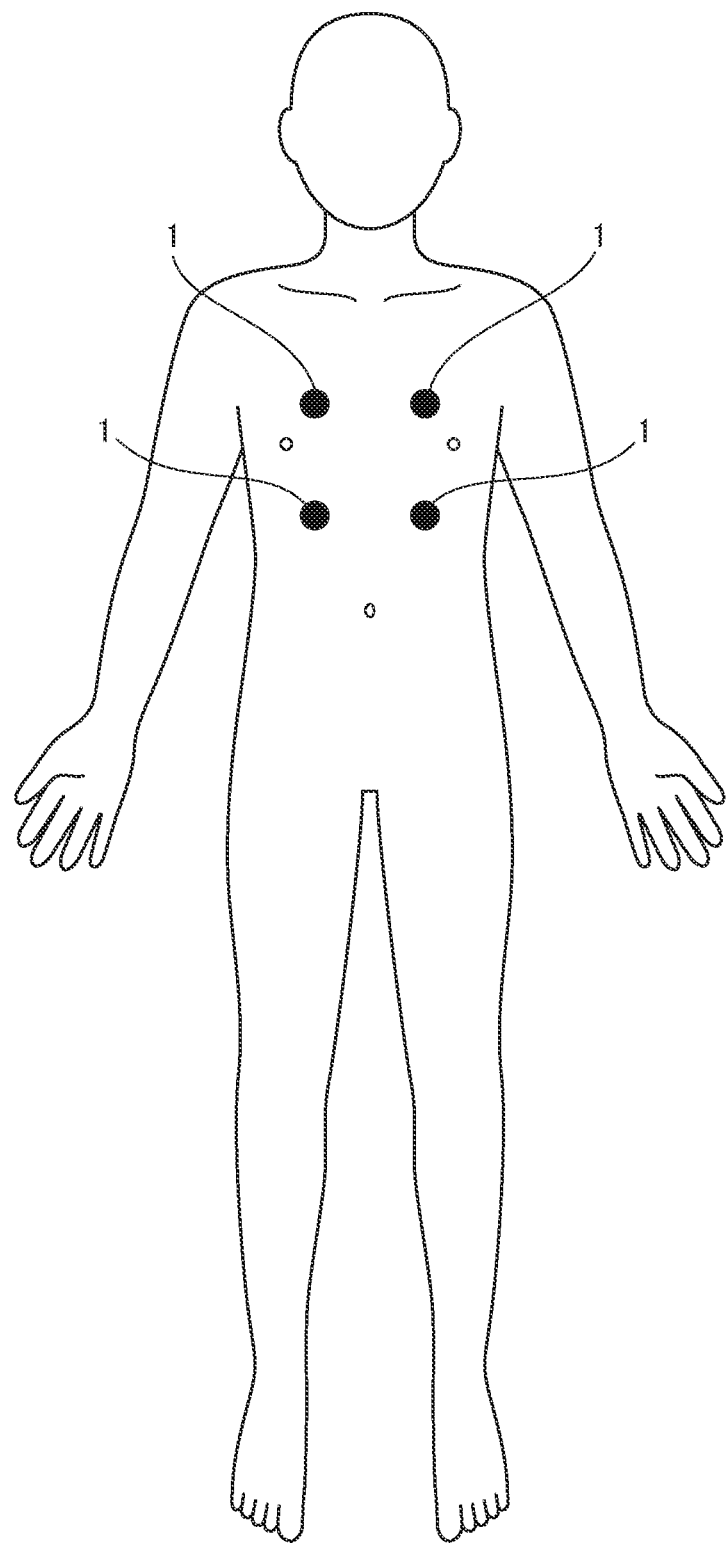
FIG. 3 is a schematic view for explaining an example of a measuring method using the position detection marker 1.

FIG. 3 is a schematic view for explaining an example of a measuring method using the position detection marker 1.

In the example illustrated in FIG. 3, an object to be measured is a human body, and the position detection marker 1 is fixed to a plurality of portions of the human body. Specifically, four position detection markers 1 are fixed to the chest. There is no particular restriction on the fixing method of the position detection marker 1, and the position detection marker 1 may be fixed by using, e.g., an adhesive tape.

In a state where the plurality of position detection markers 1 are fixed to the object to be measured, measurement using a magnetic measuring apparatus and measurement using a magnetic resonance imaging apparatus are sequentially performed. The magnetic measuring apparatus has a plurality of magnetic sensors to thereby measure magnetic field distribution in a predetermined space or plane. When performing measurement using the magnetic measuring apparatus, a cable is connected to the connector 40, and AC having a predetermined frequency is supplied to the coil 10. As a result, an AC magnetic field is generated from the coil 10. Thus, in a measured image obtained from the magnetic measuring apparatus illustrated in FIG. 4, marker points 1a are superimposed on an image P of the object to be measured. Further, when performing measurement using the magnetic resonance imaging apparatus, photographing is performed with the cable detached from the connector 40. In a measured image obtained from the magnetic resonance imaging apparatus illustrated in FIG. 4, marker points 1b are superimposed on an image Q of the object to be measured.

Figure 4:
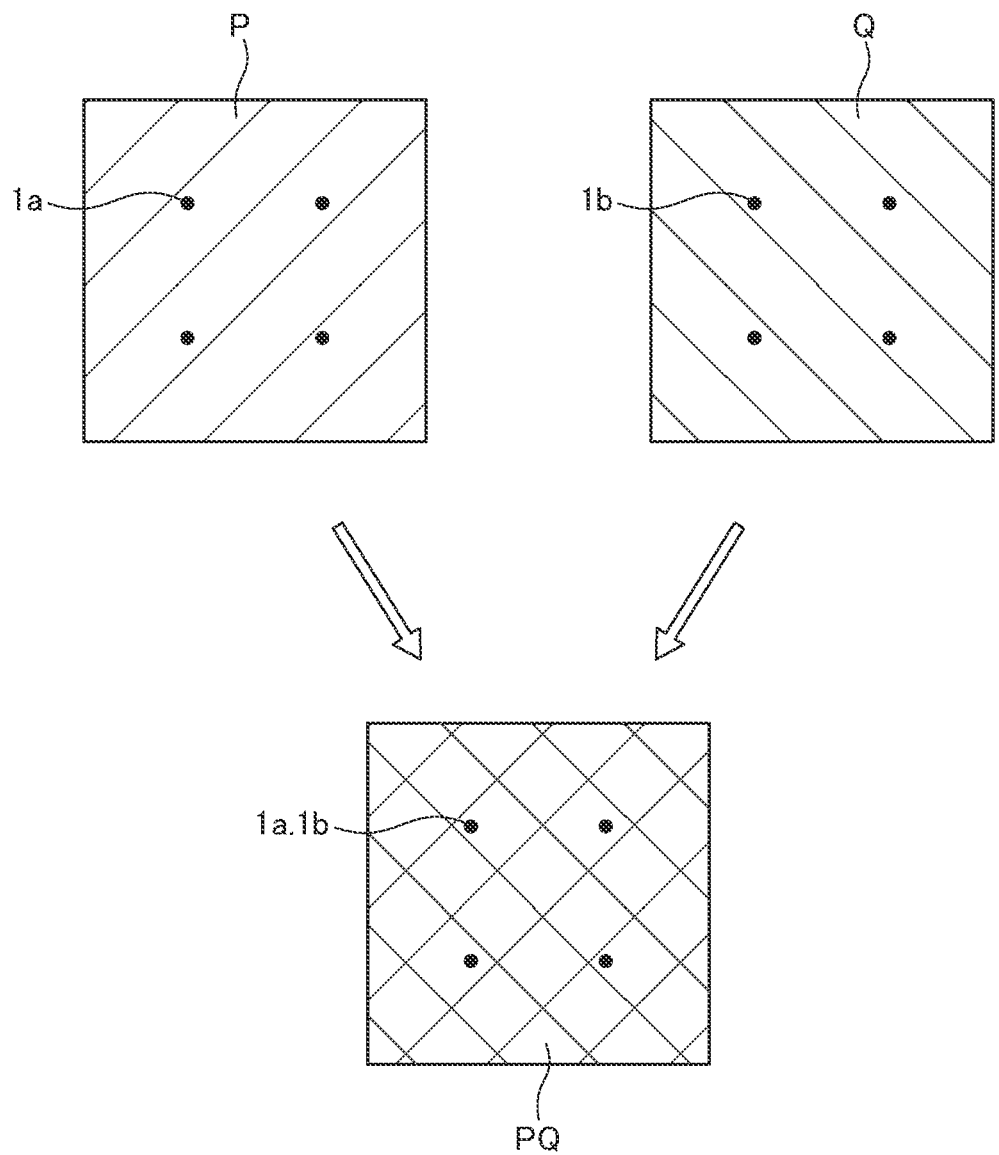
FIG. 4 is schematic view for explaining superimposing an image P on an image Q.

Then, as illustrated in FIG. 4, the images are superimposed so as to make the marker points 1a and 1b coincide with each other, thereby obtaining a synthesized image PQ in which the image P generated by the magnetic measuring apparatus and the image Q generated by the magnetic resonance imaging apparatus are superimposed accurately. Further, since the measurement using the magnetic resonance imaging apparatus is performed with the cable detached from the connector 40, the coil is in an open state, thereby preventing the coil 10 from being excessively heated by a strong magnetic field generated from the magnetic resonance imaging apparatus. Furthermore, the holding part 30 is constituted by the housing part 31 and lid part 32, and they are fixed by the screw, allowing attachment/detachment of the coil 10 and MRI marker 20. This achieves high maintainability.

Figure 5:
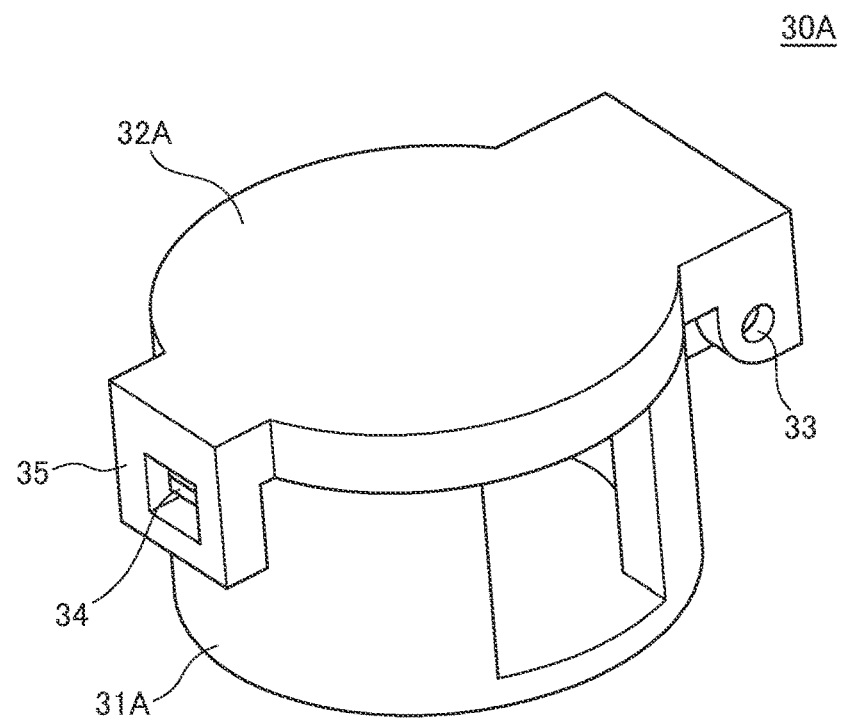
FIG. 5 is a schematic perspective view for explaining the structure of a holding part 30A according to a first modification.

FIG. 5 is a schematic perspective view for explaining the structure of a holding part 30A according to a first modification. The holding part 30A illustrated in FIG. 5 is featured in that a housing part 31A and a lid part 32A are fixed through a hinge 33 and that a claw part 34 provided in the housing part 31A is hooked on an annular part 35 provided in the lid part 32A to fix the housing part 31A and lid part 32A. This eliminates the need to use a screw, allowing a reduction in the number of components.

Figure 6:
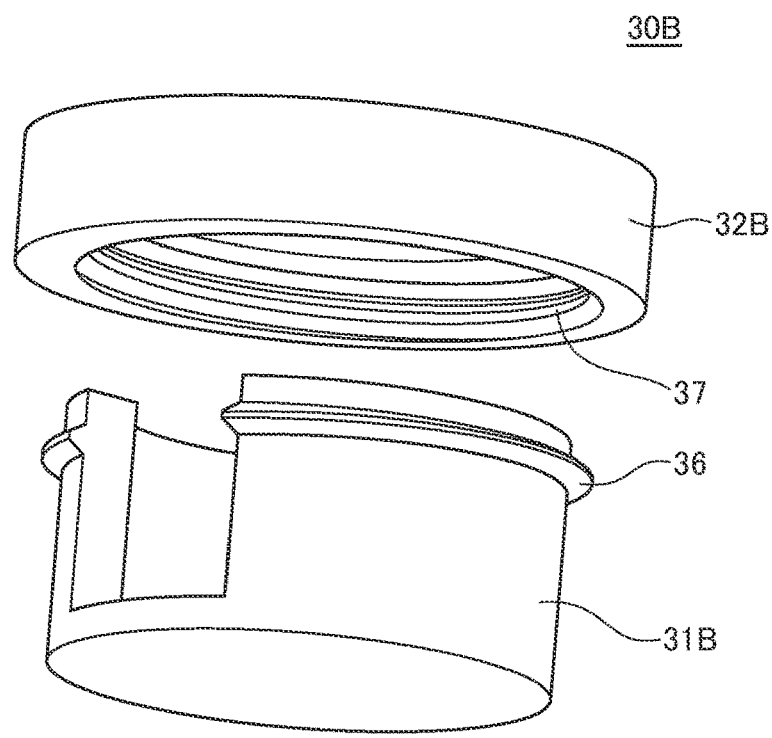
FIG. 6 is a schematic perspective view for explaining the structure of a holding part 30B according to a second modification.

FIG. 6 is a schematic perspective view for explaining the structure of a holding part 30B according to a second modification. The holding part 30B illustrated in FIG. 6 is featured in that male and female screws 36 and 37 are formed in the outer peripheral wall of a housing part 31B and the inner peripheral wall of a lid part 32B, respectively. By engaging the male and female screws 36 and 37 with each other, the housing part 31B and the lid part 32B are fixed to each other. With this configuration as well, the number of components can be reduced.

While the preferred embodiment of the present invention has been described, the present invention is not limited to the above embodiment, and various modifications may be made within the scope of the present invention, and all such modifications are included in the present invention.

For example, although a coil is used as a magnetic field source in the above embodiment, any other magnetic field source than the coil may be used as long as it generates magnetism that can be detected by the magnetic measuring apparatus. Further, although the MRI marker is disposed in the inner diameter area of the coil in the above embodiment, there is no particular restriction on the positional relation between the magnetic field source and the MRI marker as long as the relative positional relation therebetween is fixed.

What is claimed is:

1. A position detection marker comprising:
   a bobbin having a cylindrical winding core;
   a coil wound around the cylindrical winding core of the bobbin, the coil having an inner diameter and a first end and a second end, and
   a connector connected to the first and second ends of the coil and configured to enable an external cable to be selectively attached to the connector and detached from the connector, and
   an MRI marker configured to be detected by magnetic resonance imaging,
   wherein the MRI marker is configured to be inserted into the cylindrical winding core of the bobbin such that the MRI marker is disposed in the inner diameter area of the coil.

2. The position detection marker as claimed in claim 1, wherein the MRI marker is selectably attachable to the bobbin and detachable from the bobbin.

3. The position detection marker as claimed in claim 1, further comprising:
   a housing configured to house the coil and the MRI marker; and
   a lid configured to close the housing.

4. The position detection marker as claimed in claim 3, wherein the lid has an opening exposing the MRI marker.

5. The position detection marker as claimed in claim 4, wherein the MRI marker protrudes from the opening of the lid.

6. The position detection marker as claimed in claim 3, further comprising a screw that fixes the housing and the lid part.

7. The position detection marker as claimed in claim 3, wherein the housing comprises a claw that is hooked on an annular part provided in the lid.

8. The position detection marker as claimed in claim 3, wherein the housing and the lid are fixed to each other by a male screw provided in the housing that is configured to engage a female screw provided in the lid.

* * * * *